United States Patent [19]

Marsoner et al.

[11] Patent Number: 5,164,067
[45] Date of Patent: Nov. 17, 1992

[54] MEASURING DEVICE FOR DETERMINING CHEMICAL PARAMETERS OF AN AQUEOUS SAMPLE

[75] Inventors: Hermann Marsoner, Steinberg; Erich Kleinhappl; Christoph Ritter, both of Graz, all of Austria

[73] Assignee: AVL Medical Instruments AG, Schaffhausen, Switzerland

[21] Appl. No.: 427,482

[22] Filed: Oct. 27, 1989

[30] Foreign Application Priority Data

Oct. 27, 1988 [AT] Austria .................. 2660/88

[51] Int. Cl.[5] .................................. G01N 27/333
[52] U.S. Cl. .................. 204/416; 204/153.15; 204/409; 204/412; 204/414; 204/435
[58] Field of Search ........ 204/414, 409, 412, 416–420, 204/435

[56] References Cited

U.S. PATENT DOCUMENTS

| 3,151,052 | 9/1964 | Arthur et al. | 204/409 |
| 3,556,950 | 1/1971 | Dahms | 204/435 |
| 3,833,495 | 9/1974 | Grubb | 204/414 |
| 3,997,420 | 12/1976 | Buzza | 204/412 |
| 4,133,736 | 1/1979 | Nakagawa et al. | 204/415 |
| 4,235,687 | 11/1980 | Romette et al. | 204/416 |
| 4,353,789 | 10/1982 | Kashkai | 204/416 |
| 4,654,127 | 3/1987 | Baker et al. | 204/416 |
| 4,797,191 | 1/1989 | Metzner et al. | 204/409 |

Primary Examiner—T. Tung
Attorney, Agent, or Firm—Watson, Cole, Grindle & Watson

[57] ABSTRACT

In order to simplify the performance of serial measurements by means of a measuring device for determining chemical parameters of an aqueous sample, with at least one symmetrical, ion-sensitive membrane being located between the sample and an electrolytic medium and the sample and the electrolytic medium being in contact with reference electrodes connected to an evaluation unit, a measuring element is provided which can be inserted into a measuring device and which has a sample chamber connected with a reference chamber via a bore. At least one measuring chamber is provided, which is separated from the sample chamber by a symmetrical, ion-sensitive membrane. The reference chamber and all measuring chambers contain electrolytic media into which are dipped the reference electrodes located in the measuring device.

13 Claims, 3 Drawing Sheets

MEASURING DEVICE FOR DETERMINING CHEMICAL PARAMETERS OF AN AQUEOUS SAMPLE

BACKGROUND OF THE INVENTION

The invention relates to a measuring device for determining chemical parameters of an aqueous sample, with at least one symmetrical, ion-sensitive membrane located between the sample and an electrolytic medium, the sample and the electrolytic medium being in contact with identical reference electrodes connected to an evaluation unit.

DESCRIPTION OF THE PRIOR ART

The way in which conventional ion-sensitive membranes work is shown in a simplified manner in FIG. 1. The ion-sensitive membrane M contains a number of ligand molecules represented as small, incomplete circles. This symbolization reflects the fact that these ligand molecules are capable of bonding an ion, which is presented as a small circle with a + sign, or rather, as is shown schematically, of gripping it tong-like. The more tightly and precisely an ion is gripped by the ligand molecule, the more specific and selective for this particular ion the membrane will be. Such ligand molecules are mainly situated at the interface between the membrane and the electrolyte solution. The ions, i.e. the particles to be measured, are surrounded in the electrolyte solution by water molecules and are located in positions usually at a distance of several ion diameters from the membrane. In this position the intrinsic thermal energy of some ions will give them enough mobility to leave the sheath of water surrounding them and to enter the membrane just far enough to find a suitable ligand molecule. Once the ion has reached a ligand molecule it will assume a precisely defined position in it, thus being stabilized in the membrane, upon which it may be further transported within the membrane by the ligand molecule.

In ion-sensitive sensors usually both sides of the membrane are in contact with a liquid. The side of the membrane facing the inner side of a conventional electrode is in contact with the inner solution, while the outer side of the membrane is in contact with the sample. Processes of ionic exchange will thus take place on both sides of the membrane, which will keep fixed the electric charges of the ions on both sides of the membrane. In this manner a difference in electric potential will arise between the two sides of the membrane, which may be measured by conventional means.

Conventional membranes of today are fabricated in such a way that each side has somewhat different properties with regard to the density and position of the ligand molecules and their mobility within the membrane. This will result in a difference of electric potential of the two membrane sides even if they are in contact with the same electrolytic medium. This phenomenon is called the "asymmetry" of the membrane. The ideal solution, however, would be to find membranes without a potential-difference between their two sides when they are in contact with the same electrolyte solution, i.e. so-called symmetrical membranes.

Symmetrical membranes, or rather, a method of manufacturing such membranes, have been introduced recently. A major advantage of symmetrical membranes is that they do not have to be calibrated, since there is no difference in potential between their two sides when the adjoining liquids are characterized by the same ionic concentrations and activities. For example, if one side of the membrane is in contact with a standard solution and the other one with a sample, and if the potential-difference between the two sides of the membrane, or rather, the two liquids, is measured with identical reference electrodes and turns out to be zero, the sample has the same ionic concentration as the standard solution on the other side of the membrane. Since the change in electric potential is a precise function of ionic concentration, any potential-difference measured between the two sides of the membrane may be converted into a difference of the ionic concentrations of the two liquids. It is essential, however, that the two reference electrodes used for this purpose be completely identical and do not have any voltage difference relative to each other.

A known measuring device of the above type using such symmetrical, ion-sensitive membranes is shown in FIG. 2. In this instance two reference electrodes are required, i.e. R1 and R2, which are configured so as to permit sampling of the two differing sides of the membrane M. These two reference electrodes may be tested against each other to find out any difference in potential. Then the symmetrical membrane M is brought into contact with one of the two reference electrodes, R1, via a bridge electrolyte, the effective membrane surface being enlarged by using an absorbent substrate, such as a piece of filter paper F, and the sample P is placed on the other side of the membrane, which is subsequently brought into contact with the other reference electrode, R2. In this way a potential-difference between the two membrane sides is measured, from which the ionic concentration of the sample can be inferred. It will only be possible to determine the concentration of a specific type of ions for which the membrane M is selective. Unfortunately this kind of measuring device is ill-suited for measurement series as performed in laboratory work. Moreover, contamination of the device by the sample cannot be prevented.

SUMMARY OF THE INVENTION

It is an object of this invention to propose an easy-to-use measuring device utilizing the favorable properties of symmetrical, ion-selective membranes and eliminating the danger of contamination of equipment and operators.

In the invention this object is achieved by providing a measuring element that can be inserted into the measuring device, which element has a sample chamber connected to a reference chamber by means of a bore, and by providing at least one measuring chamber that is separated from the sample chamber by a symmetrical, ion-sensitive membrane, both the reference chamber and the measuring chamber containing electrolytic media in which are immersed the reference electrodes located in the measuring device. The measuring element of the device described by the invention, which may have several measuring chambers for simultaneous determination of different ions, simply is inserted into an input opening of the measuring device, whereupon the identical reference electrodes will be introduced into the reference and measuring chambers filled with an electrolytic medium and the ionic concentration will be determined via the potential-difference existing at the reference electrodes. Due to its simplicity of design the measuring element may be mass-produced cheaply, which will permit it to be treated as a one-way element to be discarded after use, together with its content. The reference electrodes are plugged into the measuring device either in the course of inserting the element itself or by a relative movement between measuring element and electrodes after insertion of the element. Since the electrodes are not in direct contact with the sample, but will only dip into the electrolytic medium in the individual chambers, the measuring device will be protected against contamination of its interior and the equipment need not be cleaned between the individual measuring cycles.

Although it is certainly possible that all measuring and reference chambers contain the same electrolytic medium, the proposal is put forward in an enhanced version of the invention that the measuring chambers contain a standard medium whereas the reference chamber be filled with a reference electrolyte, preferably KCl. The standard medium, preferably an aqueous standard solution, may contain the ions to be measured at the concentration anticipated for the sample, which will give most accurate measuring results. It is recommended here that the electrode electrolyte be used as a reference electrolyte.

It is provided in a further development of the invention that each reference electrode dipping into one of the measuring chambers be connected with a reservoir containing the standard medium, and that the reference electrode dipping into the reference chamber be connected with a reservoir containing the reference electrolyte, and that the reference electrodes have feed lines for entering the reference electrolyte or the standard medium into the reference or measuring chambers. In this variant one drop of a standard solution is filled into each measuring chamber of the measuring element just before the measuring process, and one drop of the reference electrolyte is filled into the reference chamber, into which the reference electrodes will be dipped for measurement. In the instance of reference electrodes with measuring capillaries, the electrolytic medium may be fed into the reference and measuring chambers through these capillaries. It will also be possible, however, to use solid state electrodes, such as metal/metal-chloride electrodes, which are configured as small tubes and are suitable for entering the standard medium or reference electrolyte.

A simpler configuration of the measuring device of the invention is achieved if the reference and measuring chambers of the measuring element are filled with a gel containing an electrolyte, into which are dipped solid state reference electrodes, preferably metal/metal-chloride electrodes, the reference and measuring chambers being covered by thin sheets that can be pierced by the solid state reference electrodes. In this variant no reservoirs or pumping devices are needed for the electrolytic media, as the electrolytic gel is already contained in the measuring element, which is delivered individually packaged and ready-for-use. When the sample has been entered into the sample chamber, the measuring element is introduced into the measuring device, the covering sheets are pierced by the solid state electrodes and measurement is performed.

As regards the measuring element, several design variants are possible. It is provided in a first variant that the measuring element have a sample chamber configured as a capillary tube connected to the reference and measuring chambers, which are located one behind the other, an inlet chamber for the sample being provided on one end of the capillary and an outlet chamber on the other. From the inlet chamber the sample is induced by the capillary effect to flow beneath the reference and measuring chambers and leaves the system through the outlet chamber. During its passage the sample is in contact with a number of ion-sensitive, symmetrical membranes forming the bottoms of the individual measuring chambers.

For greater ease of operation the proposal is put forward that the measuring element be provided with a handle and a cover for the individual chambers. The open measuring element is introduced into the device, where it is automatically closed at the end of the measuring process as it is ejected by the device or otherwise removed, so that it may be disposed of without any problems.

According to another variant of the invention the measuring element is configured as a one-way syringe, whose plunger chamber is used as a sample chamber, and where the reference and measuring chambers are integrated into the plunger wall and are connected to the plunger chamber. In this variant the sample withdrawal unit, for instance for taking a blood sample, is identical with the measuring element and may be inserted into the measuring device as soon as the needle has been removed.

Preferably, the syringe is provided with a locking element, which will prevent a forward motion of the syringe plunger after sample-taking, and will thus ensure that the fluid sample cannot escape.

The invention finally provides one measuring chamber each for determining Na, K and Li concentrations.

DESCRIPTION OF THE DRAWINGS

Following is a more detailed description of the invention as illustrated by the accompanying drawing, in which.

DETAILED DESCRIPTION OF PREFERRED EMBODIMENTS

Figure 1:
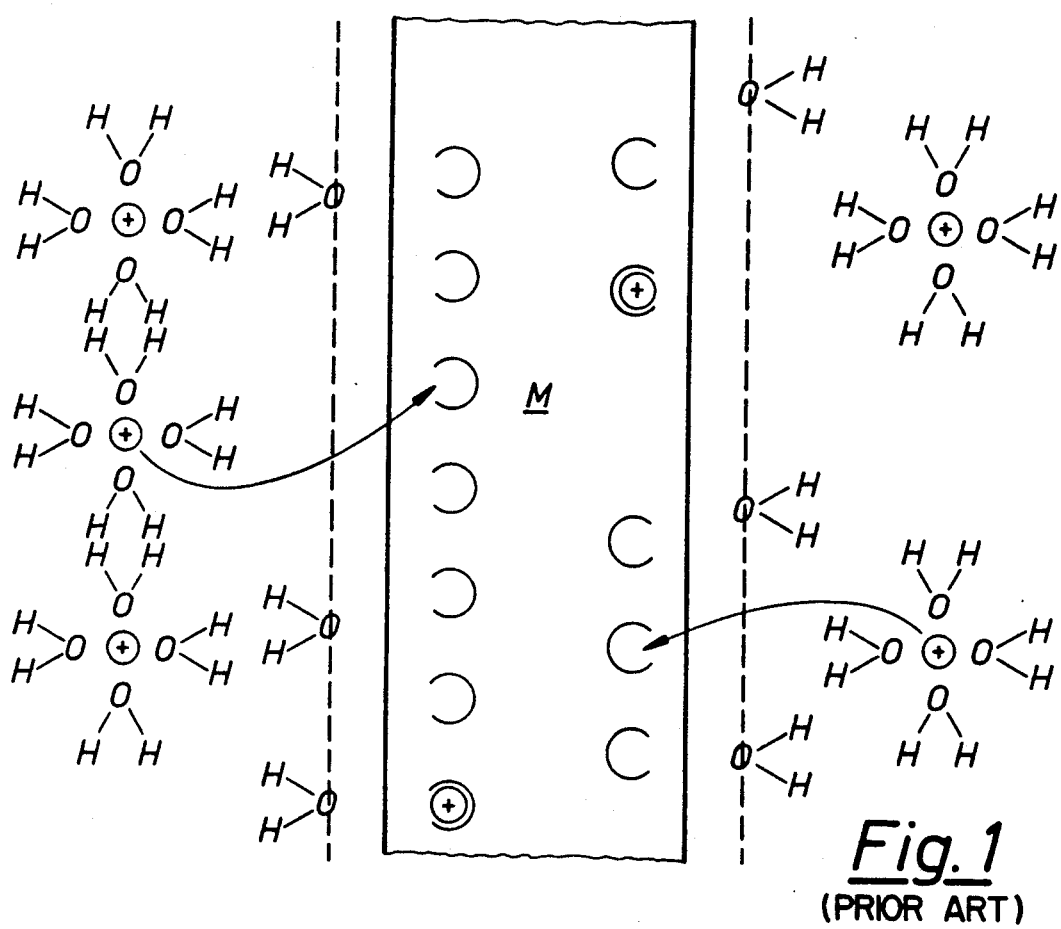
FIG. 1 shows a conventional, asymmetrical membrane.
Figure 2:
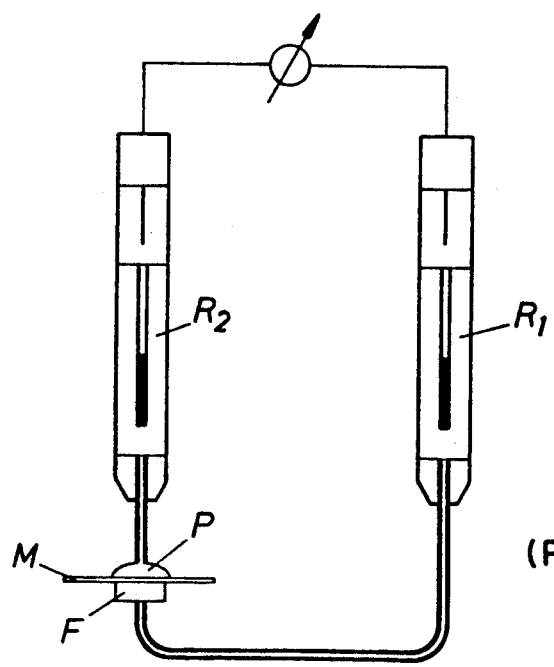
FIG. 2 presents a state-of-the-art measuring device, both figures as described at the beginning of this paper.
Figure 3:
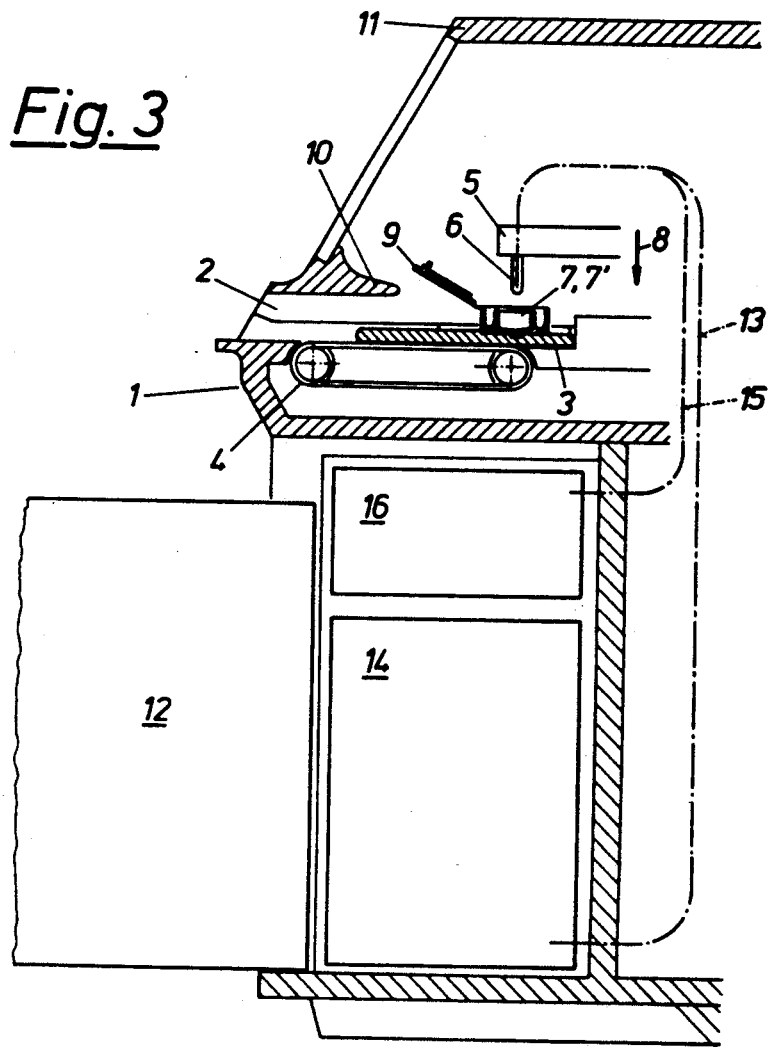
FIG. 3 shows a measuring device according to the invention, FIGS. 4a–c give various sectional views of a measuring element for the device according to FIG. 3.

FIG. 3 shows a measuring device 1 as described by the invention, with an input opening 2 through which a measuring element 3 is inserted, which element 3 is then seized by a conveyor mechanism that carries it into a measuring position. In this measuring position solid state reference electrodes 6 held by a support 5 will dip into the measuring chambers 7, which are filled with a standard medium, or into the reference chamber 7' which are filled with a reference electrolyte, the support 5 with the reference electrodes 6 performing a vertical motion in the direction indicated by arrow 8. At the end of the measuring process the measuring element 3 is removed from the measuring device 1 with the use of the conveyor mechanism 4, a nose 10 of the housing 11 of the measuring device touching the cover 9 of the measuring element 3 and closing it. The measuring element 3 is ejected and dropped into the waste container 12. The reference electrodes 6 arranged in a row which dip into the measuring chambers 7 and of which only the first one is shown in this drawing, are connected via lines 13 with a reservoir 14 for the standard medium. The same applies to the reference electrode 6 dipping into the reference chamber 7', which is connected via line 15 to a reservoir 16 for the reference electrolyte. Signal detection and evaluation, or rather, the conventional equipment required for this purpose, are not shown here in detail.

Figure 4B:
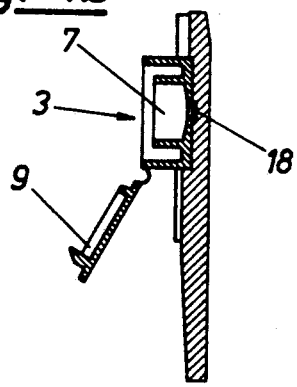
Figure 4A:
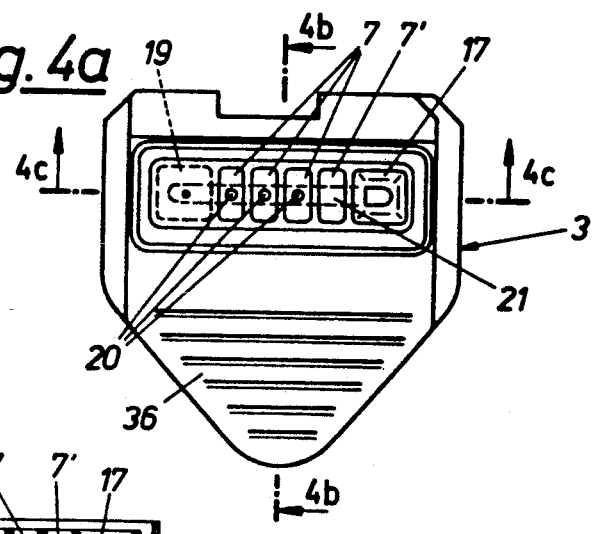
Figure 4C:
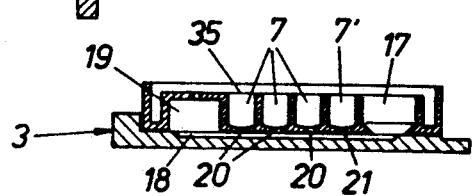

In FIGS. 4a–4c the measuring element 3 of FIG. 3 is shown in detail, i.e., in a view from above with the cover 9 removed in FIG. 4a, and as a section along line b—b with the cover 9 raised in FIG. 4b, and as a section along line c—c in FIG. 4c. In this measuring element a few drops of the sample are filled into the inlet chamber 17, from where they will flow in a capillary tube 18, or a capillary-type groove forming the sample chamber in this example, towards the outlet chamber 19, utilizing the capillary effect and passing beneath the measuring chambers 7 and the reference chamber 7'. During its passage the sample is in contact with a number of symmetrical, ion-sensitive membranes 20 (in this example for Na, K and Li), which are built into the bottom of the chambers 7 in such a way as to seal the capillary 18 towards the top. The reference chamber 7' has a small opening 21, through which the sample may be brought into contact with the reference electrode. For the purpose of measurement, one drop of the reference electrolyte is put into the reference chamber 7' and one drop of the standard solution is put into each measuring chamber 7 having an ion-sensitive membrane 20, and the reference electrodes 6 (as shown in FIG. 3) are dipped into the individual chambers 7, 7', establishing the electric contact. As above, the individual chambers 7, 7' could also be filled with an electrolytic gel and covered with a thin sheet 35, whereupon solid reference electrode tips would have to be introduced. After the measuring process the measuring element 3 can be closed with a cover 9 and may be disposed of without any leakage of sample remains or other liquids. For greater ease of handling the measuring element 3 is provided with a handle 36.

Figure 5:
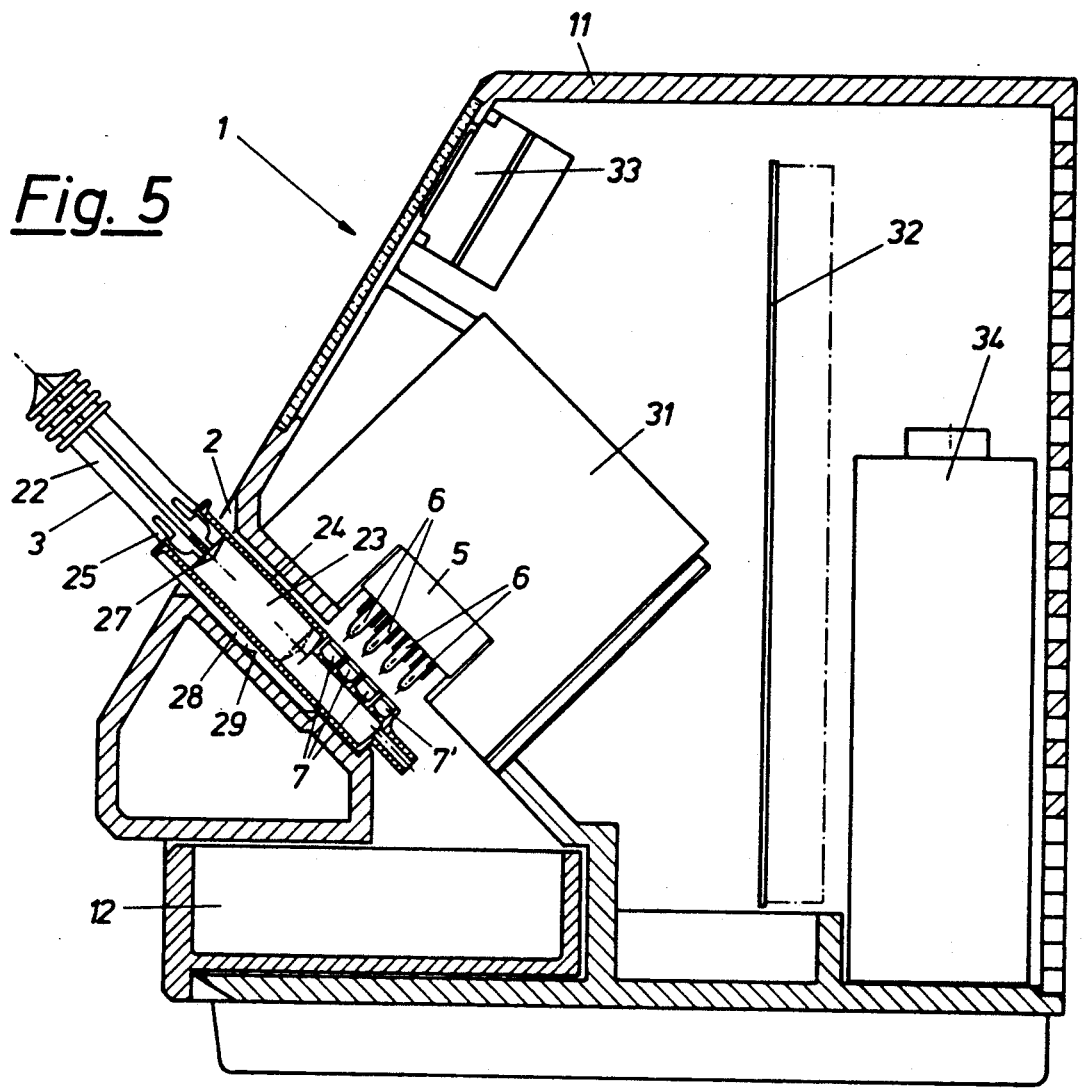
FIG. 5 shows yet another measuring device.
Figure 6:
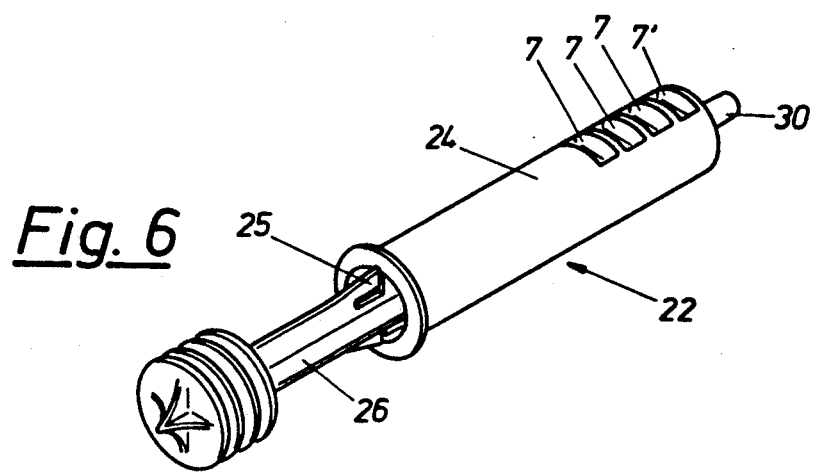
FIG. 6 presents a measuring element for the device according to FIG. 5.

In all further variants identical parts will carry identical reference numbers. In FIG. 5, for instance, a measuring device 1 is shown which contains a measuring element 3 designed as a one-way syringe 22, whose plunger chamber 23 is used as a sample chamber. In this variant the reference and measuring chambers 7, 7' are integrated in the wall 24 of the syringe 22 and are connected with the plunger chamber 23 via the membranes 20 or the opening 21 of the reference chamber 7'. As is seen in detail in FIG. 6, the syringe 22 has a locking element 25 on the shaft 26 of the plunger 27, which locks after sample-taking and will prevent the plunger 27 from moving forward. The wall 24 of the syringe 22 carries a projecting strip 28, which is guided in a groove 29 of the input opening 2 and facilitates insertion of the one-way syringe. Small quantities of the sample leaking from the fitting element 30 for the needle of the syringe 22 during measurement, are received by a removable waste container 12.

The signal output unit 31 including a pre-amplifier is directly adjacent to the support unit 5 of the reference electrodes 6. The measuring results of the individual ion concentrations, which are computed by the evaluation unit 32, are displayed by a display unit 33; the individual electrical components are supplied from a power source 34. The above variants are mainly distinguished by their compact design and small dimensions.

We claim:

1. A measuring apparatus for determining chemical parameters of an aqueous sample, comprising:
   a measuring element which defines a sample chamber, a reference chamber, at least one measuring chamber, a bore which connects said sample chamber with said reference chamber, and a symmetrical, ion-sensitive membrane separating each measuring chamber from said sample chamber, said reference chamber and said measuring chambers containing electrolytic media, and
   a measuring device in which said measuring element can be inserted, said measuring device including at least two identical reference electrodes which can be immersed in said electrolytic media in said reference chamber and each of said measuring chambers of said measuring element when positioned with said measuring device, and an evaluation unit to which said reference electrodes are connected.

2. A measuring apparatus according to claim 1, wherein each of said measuring chambers contains a standard medium and said reference chamber contains a reference electrolyte.

3. A measuring apparatus according to claim 2, wherein said reference chamber contains KCl.

4. A measuring apparatus according to claim 2, including a reservoir containing standard medium and a reservoir containing a reference electrolyte, and wherein each of said reference electrodes inserted into one of said measuring chambers is connected with said reservoir containing a standard medium and wherein said reference electrode inserted into said reference chamber is connected with a said reservoir containing a reference electrolyte, and wherein said reference electrodes have feed lines for entering said reference electrolyte and said standard medium into said reference chamber and said measuring chambers, respectively.

5. A measuring apparatus according to claim 1, wherein said reference electrodes are solid state electrodes and wherein said reference chamber and each of said measuring chambers of said measuring element are filled with a gel containing an electrolyte, into which said solid state reference electrodes can be immersed.

6. A measuring apparatus according to claim 5, wherein said solid state reference electrodes are metal/metal-chloride electrodes.

7. A measuring apparatus according to claim 5, wherein said reference chamber and each of said measuring chambers are covered by thin sheets, which are pierceable by said solid state reference electrodes.

8. A measuring apparatus according to claim 1, wherein said sample chamber of said measuring element is a capillary tube which is connected to said reference chamber and each of said measuring chambers, located one behind the other, and wherein said measuring element includes an inlet chamber for said aqueous sample on one end of said capillary tube and an outlet chamber on another end.

9. A measuring apparatus according to claim 8, wherein said measuring element is provided with a handle and with a single cover for said reference chamber and each of said measuring chambers.

10. A measuring apparatus according to claim 8, comprising three measuring chambers for determining Na, K and Li concentrations of said aqueous sample.

11. A measuring apparatus according to claim 1, wherein said measuring element is configured as a one-way syringe, comprising a plunger wall and a plunger chamber, which is used as said sample chamber, and wherein said reference chamber and each of said measuring chambers are integrated into said plunger wall and are connected to said plunger chamber.

12. A measuring apparatus according to claim 11, wherein said syringe is provided with a locking element, which prevents a forward motion of the plunger of said syringe after sample-taking.

13. A measuring apparatus according to claim 11, comprising three measuring chambers for determining Na, K and Li concentrations of said aqueous sample.

* * * * *